United States Patent [19]

Szanto et al.

[11] 3,962,426
[45] June 8, 1976

[54] ANTIBIOTICS LL-AC541 AND RACEMOMYCIN A AS TAENIACIDAL AGENTS

[75] Inventors: Joseph Szanto, Flemington; William E. Brown, Princeton; Edward Meyers, East Brunswick, all of N.J.

[73] Assignee: E. R. Squibb & Sons, Inc., Princeton, N.J.

[22] Filed: Mar. 27, 1975

[21] Appl. No.: 562,711

[52] U.S. Cl.................................. 424/116; 424/115
[51] Int. Cl.². ........................................ A61K 35/74
[58] Field of Search............................ 424/116, 115

[56] References Cited
OTHER PUBLICATIONS

Chemical Abstracts 68:98599d (1968).
Chemical Abstracts 75:112885x (1971).
Chemical Abstracts 78:38504r (1973).
Taniyama et al., J of Antibiotics, vol. 26, No. 6, June, 1971, pp. 390–392.

*Primary Examiner*—Jerome D. Goldberg
*Attorney, Agent, or Firm*—Lawrence S. Levinson; Merle J. Smith; Stephen B. Davis

[57] ABSTRACT

The antibiotics LL-AC541 and racemomycin A both members of the streptothricin family are useful as taeniacidal agents.

9 Claims, No Drawings

ANTIBIOTICS LL-AC541 AND RACEMOMYCIN A AS TAENIACIDAL AGENTS

BACKGROUND OF THE INVENTION

U.S. Pat. application Ser. No. 462,689 filed on Apr. 22, 1974 now U.S. Pat. No. 3,876,778, discloses that certain antibiotics of the streptothricin family are useful as taeniacidal agents.

SUMMARY OF THE INVENTION

This invention is directed to the discovery that two additionally antibiotics of the streptothricin family, racemomycin A and LL-AC541, are also useful as taeniacidal agents.

DETAILED DESCRIPTION OF THE INVENTION

Tapeworms cause widespread and serious infection in various animals including mammals such as dogs, cats, sheep, goats, etc., and poultry such as chickens, turkeys, etc. The infected animals represent both a health hazard as well as serious economic loss. Certain antibiotics of the streptothricin family including streptothricin, S 15-1, and 156 B-1 were disclosed as being effective taeniacidal agents in U.S. Pat. application Ser. No. 462,689. This invention is directed to the discovery that the antibiotics racemomycin A and LL-AC541, also members of the streptothricin family, are effective taeniacidal agents.

In treating animals infected with tapeworms, the antibiotics of this invention can be formulated according to conventional pharmaceutical and veterinary practice. Thus, either antibiotic or a mixture of the two antibiotics set forth above can be encapsulated with various materials such as gelatine or can be formulated as tablets, suspensions, etc., or can be mixed with a pharmaceutically acceptable carrier to form a feed supplement which can be incorporated in the animal feed in the desired concentration. The taeniacidal agents of the present invention can be combined with other parasiticides such as nematocide agents as for example dichlorvos or thiabendazole or can be combined with the taeniacidal agents disclosed in U.S. Pat. application Ser. No. 462,689.

The preferred dosage level for treating a tapeworm infection will depend to a large extent on the particular antibiotic employed, on the severity of the infection and on the particular species of animal to be treated. For example, an acceptable dose level may be higher in ruminants such as sheep than in other animals such as dogs or cats. In general, the antibiotics exhibit taeniacidal activity when administered to animals in a daily dose of about 10 to about 200 mg. per kilogram of body weight. It is preferred to employ in the range of from about 15 to about 100 mg. per kilogram of body weight per day. The antibiotics may be given in a single dose or divided into a series of smaller doses. If desired, the course of treatment may be extended over a period of days in which case the optimum daily dose level may be lowered.

The antibiotics of the present invention in the described dosages are intended to be administered orally.

The method of production of the antibiotic LL-AC541 as well as the physico-chemical and biological properties of this antibiotic are known to those skilled in the art, as note for example Zbinovsky et al., "Isolation and Characterization of Antibiotic LL-AC541," Applied Microbiology, Vol. 16, No. 4, p. 614–616 (1968), and Borders et al., "Structures of LL-AC541 and LL-AB664," Tetrahedron, Vol. 26, p. 3123–3133 (1970).

Similarly, the method of production of the antibiotic racemomycin A as well as the physico-chemical and biological properties of this antibiotic are known to those skilled in the art, as note for example Taniyama et al., "The Structure of Racemomycin A", Chem. Pharm. Bull., Vol. 10, p. 156–158 (1962) and Taniyama et al., "Characterization of Racemomycins," Chem. Pharm. Bull., Vol. 19(8), p. 1627–1634 (1971).

The following examples are illustrative of the taeniacidal properties of the antibiotics set forth above.

EXAMPLE 1

Efficacy of the Antibiotic LL-AC541 Against Hymenolepis nana in Mice

Female mice weighing 16 to 18 grams are orally inoculated with the tapeworm Hymenolepis nana. 500 plus eggs are inoculated into each mouse. Sixteen days after infection, the mice are treated for four consecutive days with a dosage of 1.5 g./kg./day by gavage of the antibiotic LL-AC541 (a crude preparation obtained by cultivating the microorganism *Streptomyces hygroscopicus* NRRL 3111, a known microorganism available from the culture collection of the Northern Regional Research Laboratories, Peoria, Illinois). The results are summarized in the following table.

| Test Compound | Dose g./kg. | Worms recovered[1] animal number | | | |
|---|---|---|---|---|---|
| | | 1 | 2 | 3 | 4 |
| control | — | + | + | + | + |
| LL-AC541 | 4×1.5 | + | + | — | — |

[1] + = no reduction
— = no worms present

EXAMPLE 2

Efficacy of the Antibiotic Racemomycin A Against Hymenolepis nana in Mice

The procedure of example 1 is followed except that the mice are treated with a dosage of 200 mg./kg./day by gavage of the antibiotic racemomycin A. The results are summarized in the following table.

| Test Compound | Dose mg./kg. | Worms recovered animal number | | | |
|---|---|---|---|---|---|
| | | 1 | 2 | 3 | 4 |
| control[1] | — | — | — | + | + |
| racemomycin A | 4 × 200 | — | — | — | — |

[1] in this experiment two of the control mice had inadequate tapeworm infection.

What is claimed is:

1. A method of treating a mammalian or poultry host infected with tapeworms which comprises orally administering to the host an effective taenicidal dose an antibiotic selected from the group consisting of LL-AC541, racemomycin A, and mixtures thereof.

2. The method of claim 1 wherein the antibiotic is LL-AC541.

3. The method of claim 1 wherein the antibiotic is racemomycin A.

4. The method of claim 1 wherein the antibiotic is encapsulated within a gelatin capsule.

5. The method of claim 1 wherein the antibiotic is formulated within a tablet or suspension.

6. The method of claim 1 wherein the antibiotic is administered in a dosage of about 15 to about 100 mg. per kilogram of body weight per day.

7. The method of claim 1 wherein the host is a dog.

8. The method of claim 1 wherein the host is a cat.

9. The method of claim 1 wherein the host is a sheep.

* * * * *